(12) United States Patent
Tallent et al.

(10) Patent No.: US 8,593,284 B2
(45) Date of Patent: Nov. 26, 2013

(54) SYSTEM AND METHOD FOR REPORTING STATUS OF A BED

(75) Inventors: Dan R. Tallent, Hope, IN (US); William Gifford Pittenger, Aurora, IN (US); Irvin J. Vanderpohl, III, Greensburg, IN (US); James L. Walke, Batesville, IN (US)

(73) Assignee: Hill-Rom Services, Inc., Batesville, IN (US)

( * ) Notice: Subject to any disclaimer, the term of this patent is extended or adjusted under 35 U.S.C. 154(b) by 1283 days.

(21) Appl. No.: 12/233,982

(22) Filed: Sep. 19, 2008

(65) Prior Publication Data

US 2010/0073168 A1  Mar. 25, 2010

(51) Int. Cl.
*G08B 23/00* (2006.01)

(52) U.S. Cl.
USPC ... 340/573.1; 340/540; 340/521; 340/286.07; 5/425; 5/616

(58) Field of Classification Search
USPC ............... 340/573.1, 573.4, 540, 575, 686.1, 340/286.07, 286.06, 665–667, 521; 5/600, 5/616, 428, 425, 618
See application file for complete search history.

(56) References Cited

U.S. PATENT DOCUMENTS

| | | | |
|---|---|---|---|
| 1,078,077 A | 11/1913 | Arnold | |
| 2,527,111 A | 10/1950 | Widrich et al. | |
| 3,325,799 A | 6/1967 | Farris | |
| 3,504,540 A | 4/1970 | Pradko et al. | |
| 3,618,592 A | 11/1971 | Stewart | |
| 3,697,846 A | 10/1972 | Mueller | |
| 3,760,794 A | 9/1973 | Basham | |
| 3,802,417 A | 4/1974 | Lang | |
| 3,826,145 A | 7/1974 | McFarland | |
| 3,836,900 A | 9/1974 | Mansfield | |
| 3,890,958 A | 6/1975 | Fister et al. | |
| 3,898,981 A | 8/1975 | Basham | |
| 3,926,177 A | 12/1975 | Hardway, Jr. et al. | |
| RE28,754 E | 3/1976 | Cook et al. | |
| 3,961,201 A | 6/1976 | Rosenthal | |
| 3,991,414 A | 11/1976 | Moran | |
| 3,991,746 A | 11/1976 | Hanna | |
| 4,020,482 A | 4/1977 | Feldl | |
| 4,038,709 A | 8/1977 | Kerwit | |
| 4,051,522 A | 9/1977 | Healy et al. | |

(Continued)

FOREIGN PATENT DOCUMENTS

| | | |
|---|---|---|
| DE | 3313843 | 10/1984 |
| DE | 3716917 | 12/1988 |

(Continued)

OTHER PUBLICATIONS

Hill-Rom, TotalCare® Bariatric Bed and TotalCare® Bariatric Plus Therapy System, Oct. 2006 User Manual (143434 REV 4) Batesville, IN.

(Continued)

*Primary Examiner* — Anh V La
(74) *Attorney, Agent, or Firm* — Kenneth C. Baran

(57) ABSTRACT

A method and system of reporting the status of a bed (12) whose occupant is at risk of an undesired event, includes indicating that the occupant is at risk of the undesired event and operating a lamp module (42) to signify a satisfactory status or an unsatisfactory status of the bed.

38 Claims, 11 Drawing Sheets

(56) References Cited

U.S. PATENT DOCUMENTS

| | | |
|---|---|---|
| 4,097,939 A | 7/1978 | Peck et al. |
| 4,172,216 A | 10/1979 | O'Shea |
| 4,175,263 A | 11/1979 | Triplett et al. |
| 4,179,692 A | 12/1979 | Vance |
| 4,183,015 A | 1/1980 | Drew et al. |
| 4,195,287 A | 3/1980 | McCoy et al. |
| 4,196,425 A | 4/1980 | Williams, Jr. et al. |
| 4,197,854 A | 4/1980 | Kasa |
| 4,228,426 A | 10/1980 | Roberts |
| 4,242,672 A | 12/1980 | Gault |
| 4,245,651 A | 1/1981 | Frost |
| 4,264,904 A | 4/1981 | McCoy et al. |
| 4,275,385 A | 6/1981 | White |
| 4,295,133 A | 10/1981 | Vance |
| 4,320,766 A | 3/1982 | Alihanka et al. |
| 4,426,884 A | 1/1984 | Polchaninoff |
| 4,435,862 A | 3/1984 | King et al. |
| 4,484,043 A | 11/1984 | Musick et al. |
| 4,539,560 A | 9/1985 | Fleck et al. |
| 4,561,440 A | 12/1985 | Kubo et al. |
| 4,565,910 A | 1/1986 | Musick et al. |
| 4,592,104 A | 6/1986 | Foster et al. |
| 4,601,356 A | 7/1986 | Muccillo, Jr. |
| 4,633,237 A | 12/1986 | Tucknott et al. |
| 4,638,307 A | 1/1987 | Swartout |
| 4,669,136 A | 6/1987 | Waters et al. |
| 4,680,790 A | 7/1987 | Packard et al. |
| 4,700,180 A | 10/1987 | Vance |
| 4,751,754 A | 6/1988 | Bailey et al. |
| 4,793,428 A | 12/1988 | Swersey |
| 4,803,744 A | 2/1989 | Peck et al. |
| 4,907,845 A | 3/1990 | Wood |
| 4,921,295 A | 5/1990 | Stollenwerk |
| 4,926,951 A | 5/1990 | Carruth et al. |
| 4,934,468 A | 6/1990 | Koerber, Sr. et al. |
| 4,953,243 A | 9/1990 | Birkmann |
| 4,953,244 A | 9/1990 | Koerber, Sr. et al. |
| 4,974,692 A | 12/1990 | Carruth et al. |
| 4,998,939 A | 3/1991 | Potthast et al. |
| 5,010,774 A | 4/1991 | Kikuo et al. |
| 5,023,967 A | 6/1991 | Ferrand |
| 5,060,174 A | 10/1991 | Gross |
| 5,115,223 A | 5/1992 | Moody |
| 5,117,521 A | 6/1992 | Foster et al. |
| 5,137,033 A | 8/1992 | Norton |
| 5,138,729 A | 8/1992 | Ferrand |
| 5,144,284 A | 9/1992 | Hammett |
| 5,161,274 A | 11/1992 | Hayes et al. |
| 5,170,364 A | 12/1992 | Gross et al. |
| 5,184,112 A | 2/1993 | Gusakov |
| 5,195,198 A | 3/1993 | Travis |
| 5,239,300 A | 8/1993 | Berger et al. |
| 5,253,656 A | 10/1993 | Rincoe et al. |
| 5,269,388 A | 12/1993 | Reichow et al. |
| 5,276,432 A | 1/1994 | Travis |
| 5,279,010 A | 1/1994 | Ferrand et al. |
| 5,317,769 A | 6/1994 | Weismiller et al. |
| 5,353,012 A | 10/1994 | Barham et al. |
| 5,377,372 A | 1/1995 | Rudolf et al. |
| 5,393,935 A | 2/1995 | Hasty et al. |
| 5,410,297 A | 4/1995 | Joseph et al. |
| 5,444,880 A | 8/1995 | Weismiller et al. |
| 5,450,639 A | 9/1995 | Weismiller et al. |
| 5,502,853 A | 4/1996 | Singleton et al. |
| 5,542,138 A | 8/1996 | Williams et al. |
| 5,561,412 A | 10/1996 | Novak et al. |
| 5,611,096 A | 3/1997 | Bartlett et al. |
| 5,633,627 A | 5/1997 | Newham |
| 5,640,145 A | 6/1997 | Newham |
| 5,654,694 A | 8/1997 | Newham |
| 5,689,839 A | 11/1997 | Laganiere et al. |
| 5,699,038 A | 12/1997 | Ulrich et al. |
| 5,713,856 A | 2/1998 | Eggers et al. |
| 5,715,548 A | 2/1998 | Weismiller et al. |
| 5,771,511 A | 6/1998 | Kummer et al. |
| 5,774,914 A | 7/1998 | Johnson et al. |
| 5,806,111 A | 9/1998 | Heimbrock et al. |
| 5,808,552 A | 9/1998 | Wiley et al. |
| 5,830,149 A | 11/1998 | Oka et al. |
| 5,838,223 A | 11/1998 | Gallant et al. |
| 5,878,452 A | 3/1999 | Brooke et al. |
| 5,906,016 A | 5/1999 | Ferrand et al. |
| 6,000,076 A | 12/1999 | Webster et al. |
| 6,008,598 A | 12/1999 | Luff et al. |
| 6,014,346 A | 1/2000 | Malone |
| 6,014,784 A | 1/2000 | Taylor et al. |
| 6,021,533 A | 2/2000 | Ellis et al. |
| 6,049,281 A | 4/2000 | Osterweil |
| 6,057,689 A | 5/2000 | Saadat |
| 6,067,019 A | 5/2000 | Scott |
| 6,078,261 A | 6/2000 | Davsko |
| 6,147,592 A * | 11/2000 | Ulrich et al. .............. 340/286.07 |
| 6,163,903 A | 12/2000 | Weismiller et al. |
| 6,166,644 A | 12/2000 | Stroda |
| 6,188,407 B1 | 2/2001 | Smith et al. |
| 6,199,508 B1 | 3/2001 | Miale et al. |
| 6,208,250 B1 | 3/2001 | Dixon et al. |
| 6,226,819 B1 | 5/2001 | Ogawa et al. |
| 6,240,579 B1 | 6/2001 | Hanson et al. |
| 6,252,512 B1 | 6/2001 | Riley |
| 6,279,183 B1 | 8/2001 | Kummer et al. |
| 6,286,166 B1 | 9/2001 | Henley et al. |
| 6,320,510 B2 | 11/2001 | Menkedick et al. |
| 6,321,878 B1 | 11/2001 | Mobley et al. |
| 6,336,235 B1 | 1/2002 | Ruehl |
| 6,351,861 B1 | 3/2002 | Shows et al. |
| 6,362,725 B1 | 3/2002 | Ulrich et al. |
| 6,377,178 B1 | 4/2002 | DeToro et al. |
| 6,378,152 B1 | 4/2002 | Washburn et al. |
| 6,396,224 B1 | 5/2002 | Luff et al. |
| 6,430,766 B1 | 8/2002 | Henley et al. |
| 6,467,111 B1 | 10/2002 | Vrzalik et al. |
| 6,473,921 B2 | 11/2002 | Brooke et al. |
| 6,481,688 B1 | 11/2002 | Welling et al. |
| 6,493,568 B1 | 12/2002 | Bell et al. |
| 6,544,200 B1 | 4/2003 | Smith et al. |
| 6,566,833 B2 | 5/2003 | Bartlett |
| 6,611,979 B2 | 9/2003 | Welling et al. |
| 6,658,680 B2 | 12/2003 | Osborne et al. |
| 6,671,905 B2 | 1/2004 | Bartlett et al. |
| RE38,419 E | 2/2004 | Auer et al. |
| 6,691,346 B2 | 2/2004 | Osborne et al. |
| 6,761,344 B2 | 7/2004 | Welling et al. |
| 6,771,172 B1 | 8/2004 | Robinson et al. |
| 6,771,181 B1 | 8/2004 | Hughen, Jr. |
| 6,781,517 B2 | 8/2004 | Moster et al. |
| 6,791,460 B2 | 9/2004 | Dixon et al. |
| 6,819,254 B2 | 11/2004 | Riley |
| 6,822,571 B2 | 11/2004 | Conway |
| 6,829,796 B2 | 12/2004 | Salvatini et al. |
| 6,863,652 B2 | 3/2005 | Huang et al. |
| 6,876,303 B2 | 4/2005 | Reeder et al. |
| 6,880,189 B2 | 4/2005 | Welling et al. |
| 6,892,405 B1 | 5/2005 | Dimitriu et al. |
| 6,897,780 B2 | 5/2005 | Ulrich et al. |
| 6,957,461 B2 | 10/2005 | Osborne et al. |
| 6,978,500 B2 | 12/2005 | Osborne et al. |
| 6,982,405 B2 | 1/2006 | Erickson et al. |
| 7,010,369 B2 | 3/2006 | Borders et al. |
| 7,014,000 B2 | 3/2006 | Kummer et al. |
| 7,017,208 B2 | 3/2006 | Weismiller et al. |
| 7,038,588 B2 | 5/2006 | Boone et al. |
| 7,055,195 B2 | 6/2006 | Roussy |
| 7,100,222 B2 | 9/2006 | Metz et al. |
| 7,154,397 B2 | 12/2006 | Zerhusen et al. |
| 7,155,317 B1 | 12/2006 | Tran |
| 7,171,708 B2 | 2/2007 | Osborne et al. |
| 7,200,882 B2 | 4/2007 | Heimbrock |
| 7,237,287 B2 | 7/2007 | Weismiller et al. |
| 7,242,308 B2 | 7/2007 | Ulrich et al. |
| 7,253,366 B2 | 8/2007 | Bhai |
| 7,296,312 B2 | 11/2007 | Menkedick et al. |
| 7,315,535 B2 | 1/2008 | Schuman |
| 7,319,386 B2 | 1/2008 | Collins, Jr. et al. |

(56) References Cited

U.S. PATENT DOCUMENTS

| | | |
|---|---|---|
| 7,330,127 B2 | 2/2008 | Price et al. |
| 7,406,731 B2 | 8/2008 | Menkedick et al. |
| 7,437,787 B2 | 10/2008 | Bhai |
| 7,443,302 B2 | 10/2008 | Reeder et al. |
| 7,454,805 B2 | 11/2008 | Osborne et al. |
| 7,472,439 B2 | 1/2009 | Lemire et al. |
| 7,480,951 B2 | 1/2009 | Weismiller et al. |
| 7,506,390 B2 | 3/2009 | Dixon et al. |
| 7,515,059 B2 | 4/2009 | Price et al. |
| 7,520,006 B2 | 4/2009 | Menkedick et al. |
| 7,533,429 B2 | 5/2009 | Menkedick et al. |
| 7,538,659 B2 | 5/2009 | Ulrich et al. |
| 7,557,718 B2 | 7/2009 | Petrosenko et al. |
| 7,568,246 B2 | 8/2009 | Weismiller et al. |
| 7,594,286 B2 | 9/2009 | Williams |
| 7,610,637 B2 | 11/2009 | Menkedick et al. |
| 7,657,956 B2 | 2/2010 | Stacy et al. |
| 7,669,263 B2 | 3/2010 | Menkedick et al. |
| 7,676,866 B2 | 3/2010 | Toms et al. |
| 7,679,520 B2 | 3/2010 | Zerhusen et al. |
| 7,690,059 B2 | 4/2010 | Lemire et al. |
| 7,703,158 B2 | 4/2010 | Wilker, Jr. et al. |
| 7,716,762 B2 | 5/2010 | Ferraresi et al. |
| 7,746,218 B2 | 6/2010 | Collins, Jr. et al. |
| 7,761,942 B2 | 7/2010 | Benzo et al. |
| 7,779,493 B2 | 8/2010 | Lemire et al. |
| 7,805,784 B2 | 10/2010 | Lemire et al. |
| 7,834,768 B2 | 11/2010 | Dixon et al. |
| 7,836,531 B2 | 11/2010 | Girard et al. |
| 7,861,334 B2 | 1/2011 | Lemire et al. |
| 7,962,981 B2 | 6/2011 | Lemire et al. |
| 7,978,084 B2 | 7/2011 | Dixon et al. |
| 8,117,701 B2 | 2/2012 | Bobey et al. |
| 2001/0011393 A1 | 8/2001 | Brooke et al. |
| 2001/0032362 A1 | 10/2001 | Welling et al. |
| 2002/0002742 A1 | 1/2002 | Osborne et al. |
| 2002/0044059 A1 | 4/2002 | Reeder et al. |
| 2002/0066142 A1 | 6/2002 | Osborne et al. |
| 2002/0138905 A1 | 10/2002 | Bartlett et al. |
| 2002/0151990 A1 | 10/2002 | Ulrich et al. |
| 2003/0061664 A1 | 4/2003 | Salvatini et al. |
| 2003/0197614 A1 | 10/2003 | Smith et al. |
| 2004/0034936 A1 | 2/2004 | Welling et al. |
| 2004/0103475 A1 | 6/2004 | Ogawa et al. |
| 2004/0122476 A1 | 6/2004 | Wung |
| 2004/0128765 A1 | 7/2004 | Osborne et al. |
| 2004/0130452 A1 | 7/2004 | Cherubini |
| 2004/0175289 A1 | 9/2004 | Takizawa et al. |
| 2004/0177443 A1 | 9/2004 | Simmonds et al. |
| 2004/0177445 A1 | 9/2004 | Osborne et al. |
| 2004/0227737 A1 | 11/2004 | Novak et al. |
| 2005/0035871 A1 | 2/2005 | Dixon et al. |
| 2005/0137530 A1 | 6/2005 | Campbell et al. |
| 2005/0165325 A1 | 7/2005 | Hornig |
| 2005/0166324 A1 | 8/2005 | Dixon et al. |
| 2005/0172405 A1 | 8/2005 | Menkedick et al. |
| 2005/0187463 A1 | 8/2005 | Quistgaard et al. |
| 2005/0188462 A1 | 9/2005 | Heimbrock |
| 2005/0219059 A1 | 10/2005 | Ulrich et al. |
| 2006/0049936 A1 | 3/2006 | Collins et al. |
| 2006/0053555 A1 | 3/2006 | Poulos et al. |
| 2006/0075560 A1 | 4/2006 | Osborne et al. |
| 2006/0096029 A1 | 5/2006 | Osborne et al. |
| 2006/0101581 A1 | 5/2006 | Blanchard et al. |
| 2006/0117482 A1 | 6/2006 | Branson |
| 2006/0162079 A1 | 7/2006 | Menkedick et al. |
| 2006/0168730 A1 | 8/2006 | Menkedick et al. |
| 2006/0168731 A1 | 8/2006 | Menkedick et al. |
| 2006/0271207 A1 | 11/2006 | Shaw |
| 2006/0277683 A1 | 12/2006 | Lamire et al. |
| 2007/0076852 A1 | 4/2007 | Ichikawa et al. |
| 2007/0130692 A1 | 6/2007 | Lemire et al. |
| 2007/0156031 A1 | 7/2007 | Sullivan et al. |
| 2007/0157385 A1 | 7/2007 | Lemire et al. |
| 2007/0163043 A1 | 7/2007 | Lemire et al. |
| 2007/0163045 A1 | 7/2007 | Becker et al. |
| 2007/0164871 A1 | 7/2007 | Dionne et al. |
| 2007/0169268 A1 | 7/2007 | Lemire et al. |
| 2007/0174964 A1 | 8/2007 | Lemire et al. |
| 2007/0174965 A1 | 8/2007 | Lemire et al. |
| 2007/0180616 A1 | 8/2007 | Newkirk et al. |
| 2007/0210917 A1 | 9/2007 | Collins, Jr. et al. |
| 2007/0268480 A1 | 11/2007 | Kaye |
| 2008/0005838 A1 | 1/2008 | Wan Fong et al. |
| 2008/0010747 A1 | 1/2008 | Dixon et al. |
| 2008/0010748 A1 | 1/2008 | Menkedick et al. |
| 2008/0169931 A1 | 7/2008 | Gentry et al. |
| 2008/0172789 A1 | 7/2008 | Elliot et al. |
| 2008/0201847 A1 | 8/2008 | Menkedick et al. |
| 2008/0201851 A1 | 8/2008 | Menkedick et al. |
| 2008/0205311 A1 | 8/2008 | Perkins et al. |
| 2008/0235872 A1 | 10/2008 | Newkirk et al. |
| 2008/0289108 A1 | 11/2008 | Menkedick et al. |
| 2009/0031498 A1 | 2/2009 | Girard et al. |
| 2009/0089930 A1 | 4/2009 | Benzo et al. |
| 2009/0094744 A1 | 4/2009 | Benzo et al. |
| 2009/0094745 A1 | 4/2009 | Benzo et al. |
| 2009/0094746 A1 | 4/2009 | Ferraresi et al. |
| 2009/0237264 A1 | 9/2009 | Bobey et al. |
| 2009/0302782 A1 | 12/2009 | Smith |
| 2009/0313758 A1 | 12/2009 | Menkedick et al. |
| 2010/0000018 A1 | 1/2010 | Eleonori et al. |
| 2010/0052917 A1 | 3/2010 | Sullivan et al. |
| 2010/0073168 A1 | 3/2010 | Tallent et al. |
| 2010/0275376 A1 | 11/2010 | Benzo et al. |
| 2011/0037597 A1 | 2/2011 | Dixon et al. |
| 2011/0162141 A1 | 7/2011 | Lemire et al. |
| 2011/0231996 A1 | 9/2011 | Lemire et al. |
| 2011/0277242 A1 | 11/2011 | Dionne et al. |

FOREIGN PATENT DOCUMENTS

| | | |
|---|---|---|
| EP | 0 860 803 | 8/1998 |
| EP | 1199027 | 4/2002 |
| EP | 1354539 | 10/2003 |
| EP | 1477110 | 11/2004 |
| JP | 2-156950 | 6/1990 |
| JP | 02-141441 | 11/1990 |
| JP | 03-047860 | 2/1991 |
| JP | 7107195 | 4/1995 |
| JP | 11290395 | 4/1999 |
| JP | 11299837 | 11/1999 |
| JP | 2003-164496 | 6/2003 |
| JP | 2003-524483 | 8/2003 |
| JP | 2004049706 A | 1/2004 |
| JP | 2004-49706 | 2/2004 |
| JP | 2004-141484 | 5/2004 |
| JP | 2005-118147 | 5/2005 |
| JP | 2005-168913 | 6/2005 |
| JP | 2005168913 A | 6/2005 |
| JP | 2005185346 | 7/2005 |
| WO | WO 97/20534 | 6/1997 |
| WO | 01/47340 | 7/2001 |
| WO | WO 0175834 | 10/2001 |
| WO | WO 0185085 | 11/2001 |
| WO | WO 2004093023 | 10/2004 |
| WO | 2007056342 A2 | 5/2007 |
| WO | WO 2007056342 A2 | 5/2007 |
| WO | 2009056764 A1 | 5/2009 |

OTHER PUBLICATIONS

Stryker, "Critical Care Beds InTouch: Stryker" http://www.stryker.com/en-us/products/PatientHandlingEMSandEvacuationEquipment/Beds/CriticalCareBeds/InTouch/006724, Date: Unknown.

European Search Report, "Application No. EP 09252218", (Dec. 5, 2011), Berlin.

Australian official action from related AU 2006268288, dated Oct. 18, 2011, 2 pages.

Official action for AU 2006268288 dated Dec. 8, 2010, 3 pages.

Official action (in Japanese and English language translation) for JP 2008-520446 dated Jul. 26, 2011, 8 pages.

(56) References Cited

OTHER PUBLICATIONS

PCT International Search Report for PCT/US2006/026788 completed by the US Searching Authority on Apr. 3, 2007.
Centra From Hill-Rom, Hill-Rom 1992.
In Services Manual Centra Bed from Hill-Rom, Hill-Rom 1996.
The Advance 2000 Bed from Hill-Rom, Hill-Rom 1993.
ProAxis® Plus Bed User Manual, 138675, Hill-Rom, p. 3-1.
DuoDeteq™ Alternating Therapy System User Manual, (US037), Hill-Rom, pp. 14 through 16.
Adel 500XL Childbearing Bed, Stryker Patient Care, May 1995.
Stryker Adel 2100EC Childbearing Bed, Stryker Patient care, Jan. 1994.
Advantage Stretcher Stryker Patient Handling, May 1994.
Hausted Gemini Series, Hausted, Inc., Oct. 1993.
Stryker Adel 500XL Childbearing Bed Service Manual, Adel Medical Ltd. 1986.
Silenzio, Silenzio. Plus, Silenzio, Delta, Nasal CPAP System, Operator's Guide, Jun. 2003.
Gaymar, Aire Twin, Alternating Pressure and Low-Air-Loss Therapy Mattress Replacement Systems, Operator's Manual, 2005.
Hill-Rom, User Manual TotalCare® Bariatric Bed, Product No. P1830A, Apr. 2003.

\* cited by examiner

SYSTEM AND METHOD FOR REPORTING STATUS OF A BED

TECHNICAL FIELD

The subject matter described herein relates to methods and systems for reporting the status of a bed, such as a hospital bed.

BACKGROUND

Non-residential beds are used in hospitals, private residences and other facilities. These beds include special features such as brakes, head end and foot end siderails and adjustable elevation. The occupant of these types of beds is typically a patient who may be vulnerable to adverse events such as falls. Safeguards can be used to help mitigate the risk to the vulnerable patient. For example, a patient vulnerable to falling can be better protected if the brakes on the bed are set, the bed is at its lowest elevation and at least the head end siderails are deployed. It is desirable to indicate whether or not such safeguards are in place either to convey confidence that the bed is in the desired state or to provoke corrective action if the bed is not in the desired state. The present application discloses a method and system for making such indications.

SUMMARY

A method for reporting the status of a bed whose occupant is at risk of an undesired event includes indicating that the occupant is at risk of the undesired event and operating a lamp module to signify a satisfactory status or an unsatisfactory status of the bed in response to the risk indication and an indication of whether or not a risk related safeguard is in effect.

The foregoing and other features of the various embodiments of the method and associated systems will become more apparent from the following detailed description and the accompanying drawings.

DETAILED DESCRIPTION

Figure 1:
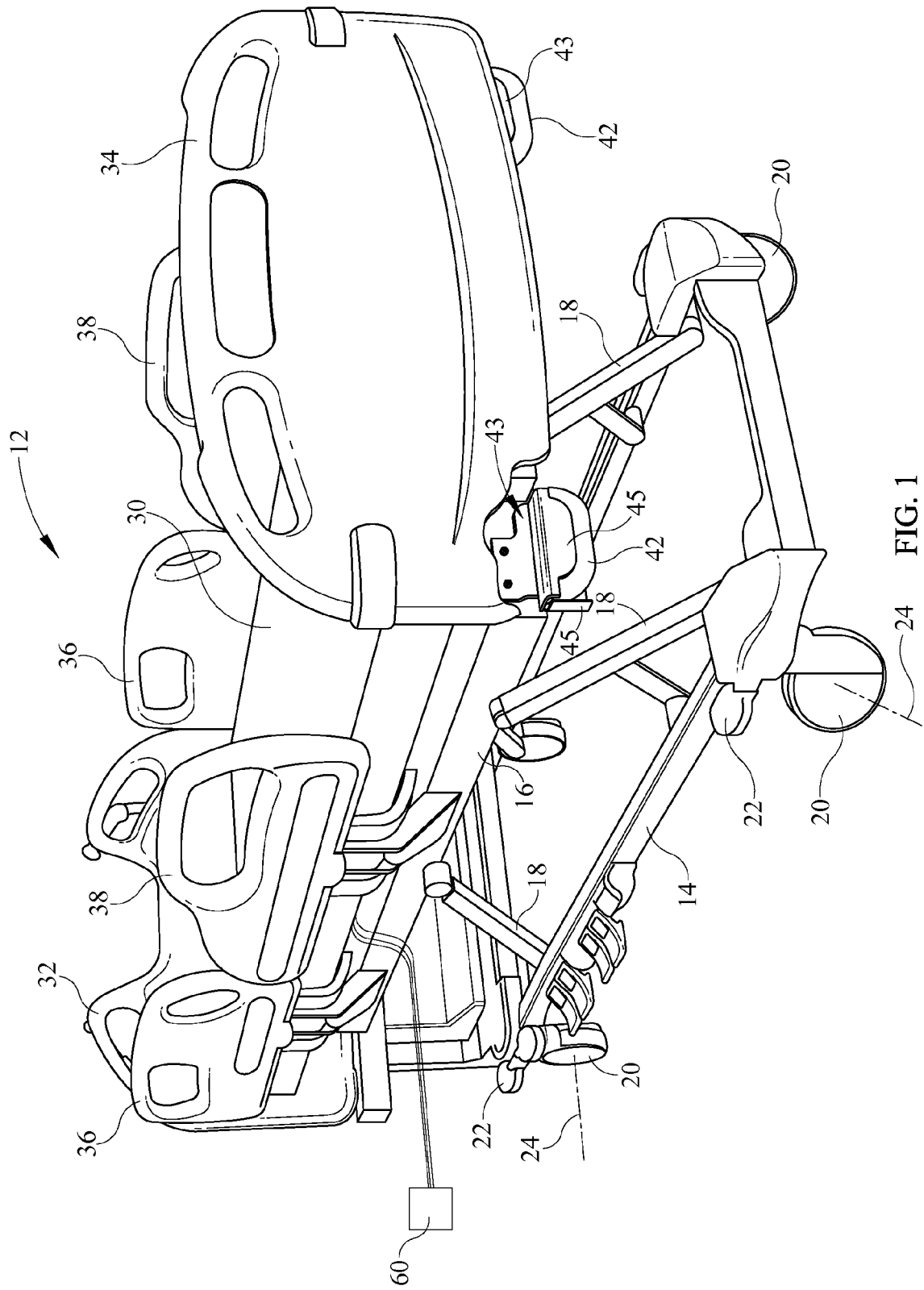
FIG. 1 is a perspective view of a hospital bed.
Figure 2:
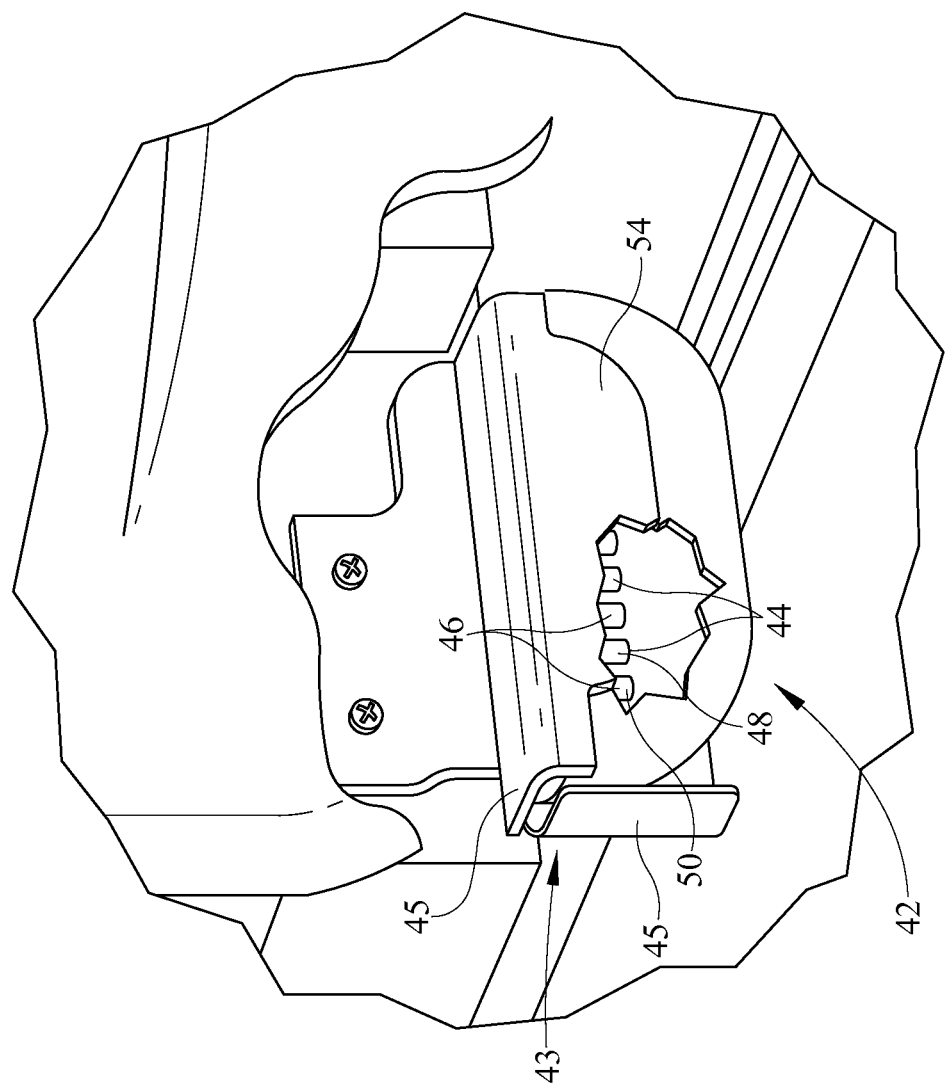
FIG. 2 is an enlarged view of a portion of the bed of FIG. 1.

Referring to FIGS. 1 and 2, a bed 12 of the type used for hospital patients includes a base frame 14, a height adjustable frame 16 and a set of links 18, which are part of a system for adjusting the height adjustable frame between lowest and highest elevations. The base frame includes wheels 20 and a brake system controlled by foot pedals 22 for preventing rotation of at least one of the wheels about its rotational axis 24. A variety of brake systems and a variety of height adjustment systems are satisfactory for use with the methods and systems disclosed herein.

Figure 3:
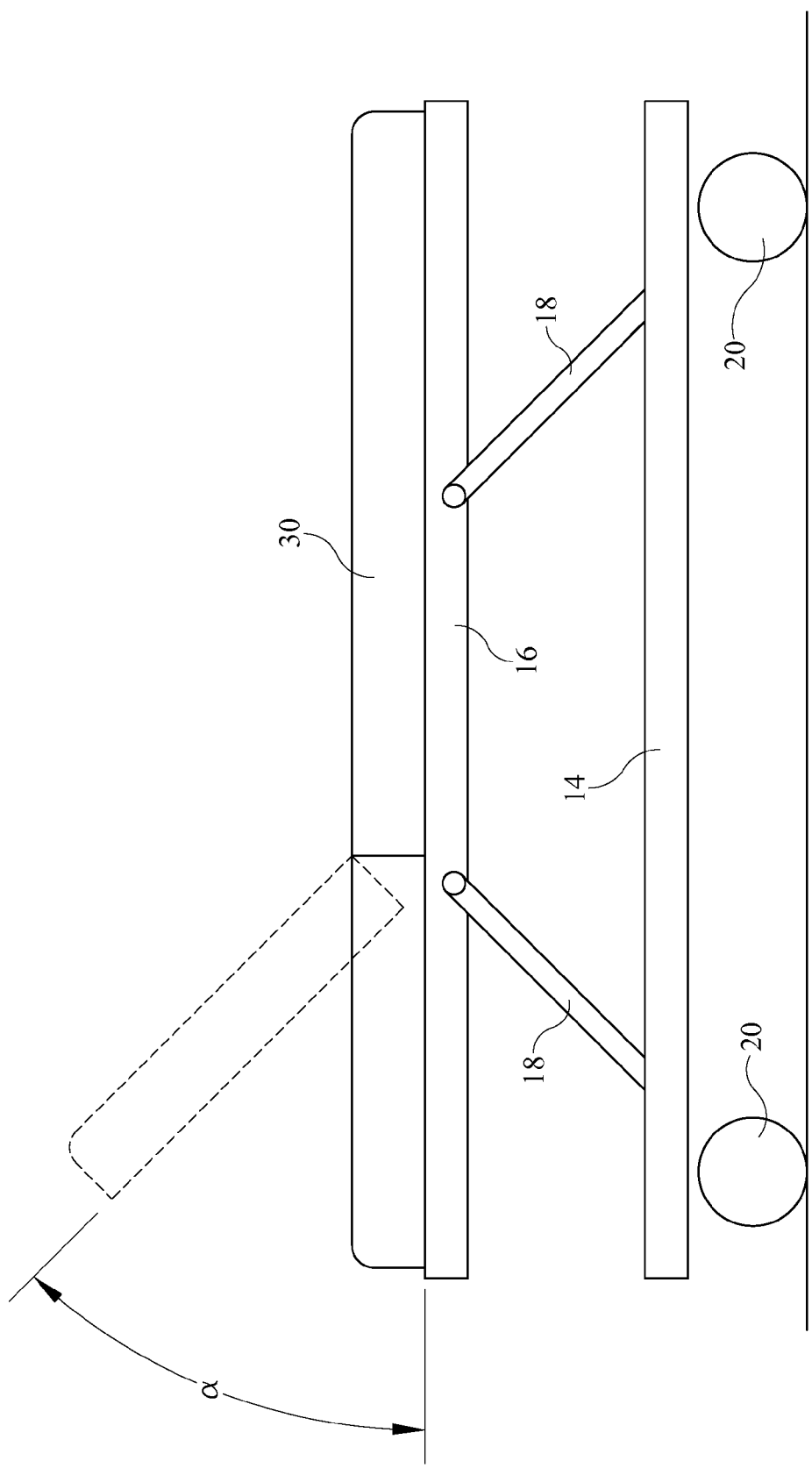
FIG. 3 is a schematic, side elevation view of the bed.

The bed also includes a mattress 30 atop the adjustable frame, a headboard 32, and a footboard 34. The adjustable frame supports a set of laterally spaced apart head end siderails 36 and a set of laterally spaced apart foot end siderails 38. The siderails may be deployed, as shown in the illustration, or may be retracted to a lower position or removed to facilitate ingress or egress of a bed occupant or to provide easy access to the occupant by a caregiver. As shown schematically in FIG. 3, the head end of the bed maybe pivotable such that it can be oriented at a Head of Bed (HOB) angle α.

Figure 6:
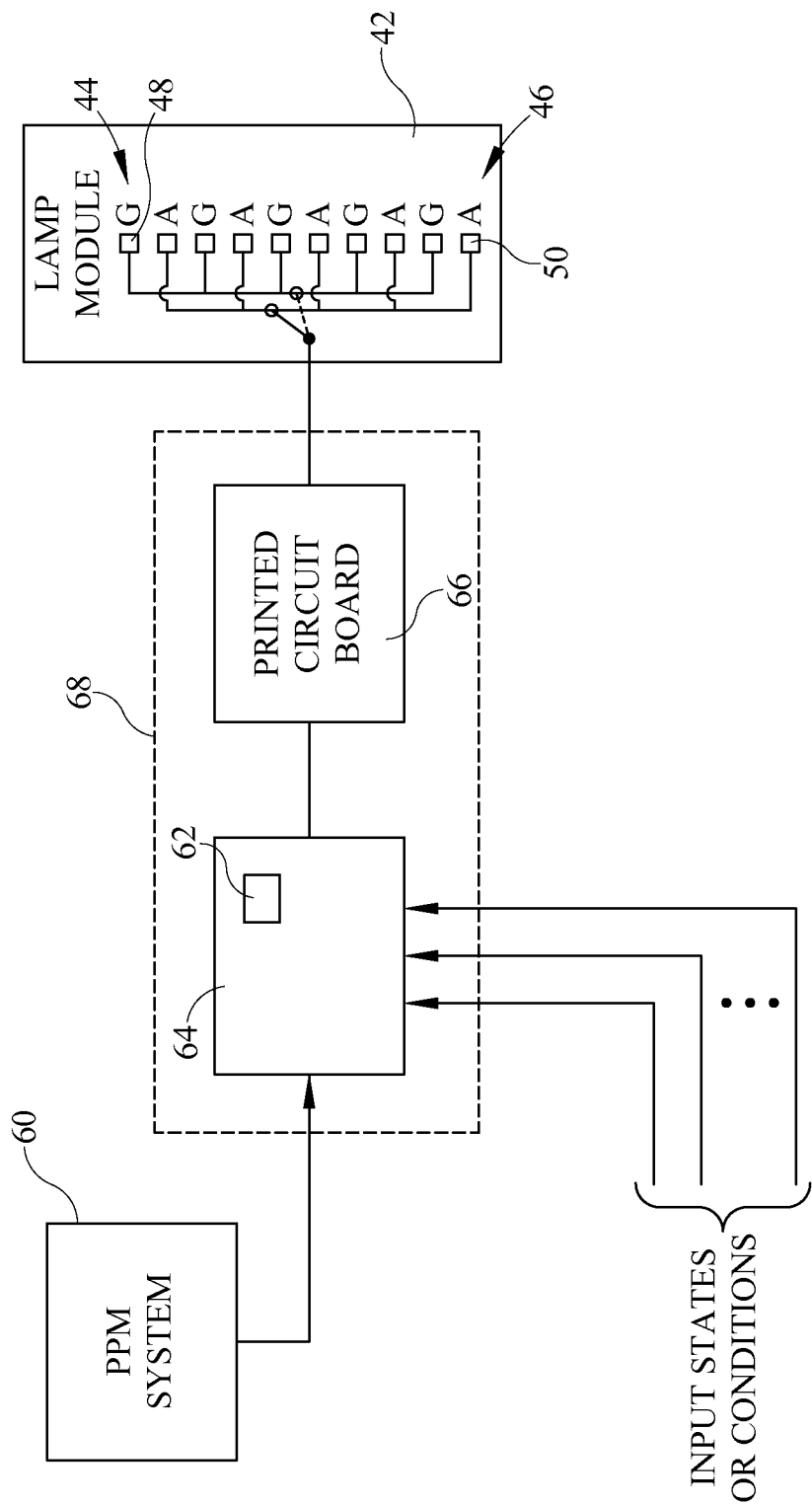
FIG. 6 is a schematic view showing certain components of a physical system for reporting the status of the bed.

At least one lamp module 42 is also secured to the height adjustable frame by left and right brackets 43 having shield portions 45. As seen in FIGS. 2 and 6, an exemplary lamp module comprises two arrays 44, 46 of light emitters such as light emitting diodes (LED's) 48, 50 housed behind a translucent or transparent protective lens 54. The lamp module is positioned and oriented relative to the frame and brackets so that light emitted from the module is directed predominantly or at least partially toward the floor. This helps reduce annoyance to occupants of nearby beds when the light is on. However, because the light shines toward the floor, the illumination of the floor and any reflection off the floor will help capture the attention of a caregiver in the vicinity. The shield portions 45 of the bracket shield the lamp module from damage and help intercept light emission in directions that would annoy occupants of nearby beds. The LED arrays emit light having different properties. For example, the LED's 48 of array 44 emit visible green light and the LED's 50 of array 46 emit visible amber light. Either or both arrays may be controlled to produce steady or intermittent (non-steady) light emission. As seen best in FIG. 6, the arrays are arranged so that their individual members alternate.

The bed also includes a Patient Position Monitoring (PPM) system shown schematically as 60. The PPM system has an armed state which is used when it is desired to monitor the position and/or activity of the bed occupant. For example, the PPM system may be armed when the occupant is judged to have an unacceptably high risk of falling or when the occupant is not authorized to exit from the bed without assistance. A typical armed PPM system has three sensitivity levels, one to annunciate an alert when the occupant has moved, one to annunciate an alert if the occupant has moved in a way that suggests an intent to exit the bed and one to annunciate an alert if the occupant has exited the bed.

For an occupant judged to be a fall risk, the states of the brake, the height adjustable frame 16, and the head end siderails 36 may be designated as states or conditions of the bed related to the fall risk. Individually, these states or conditions are input conditions that determine whether or not a safeguard related to the risk is in effect. Collectively, these states define a safeguard related to fall risk. The safeguard can be in effect or not depending on whether or not the associated input conditions are satisfied. For example, the brake being set, the height adjustable frame being at its lowest position and the head end siderails being deployed are relatively safe states of the brake, height adjustable frame and head end siderails respectively for an occupant judged to be a fall risk. By contrast, the brake being released, the height adjustable frame being higher than its lowest position and the head end siderails being retracted or removed are relatively less safe states for that occupant. Preferably, all of the desired conditions must be satisfied (brake set, height adjustable frame at its lowest position, both head end siderails deployed) to declare that the safeguard is in effect. If even one of the desired input conditions is not satisfied, the safeguard is not in effect. Alternatively, the safeguard may be declared to be in effect if even one of the desired conditions is present. Only if all the desired conditions are absent is the safeguard considered to not be in effect.

The above described condition relating to deployment of the siderails is configurable by the user. Specifically, the user can specify that all four siderails must be deployed or that both head end siderails and either foot end siderail must be deployed in order for the siderails to be considered to be in a desired state. Other variations on the individual condition or conditions and other combinations of conditions fall within the scope of the subject matter claimed herein.

Figure 4:
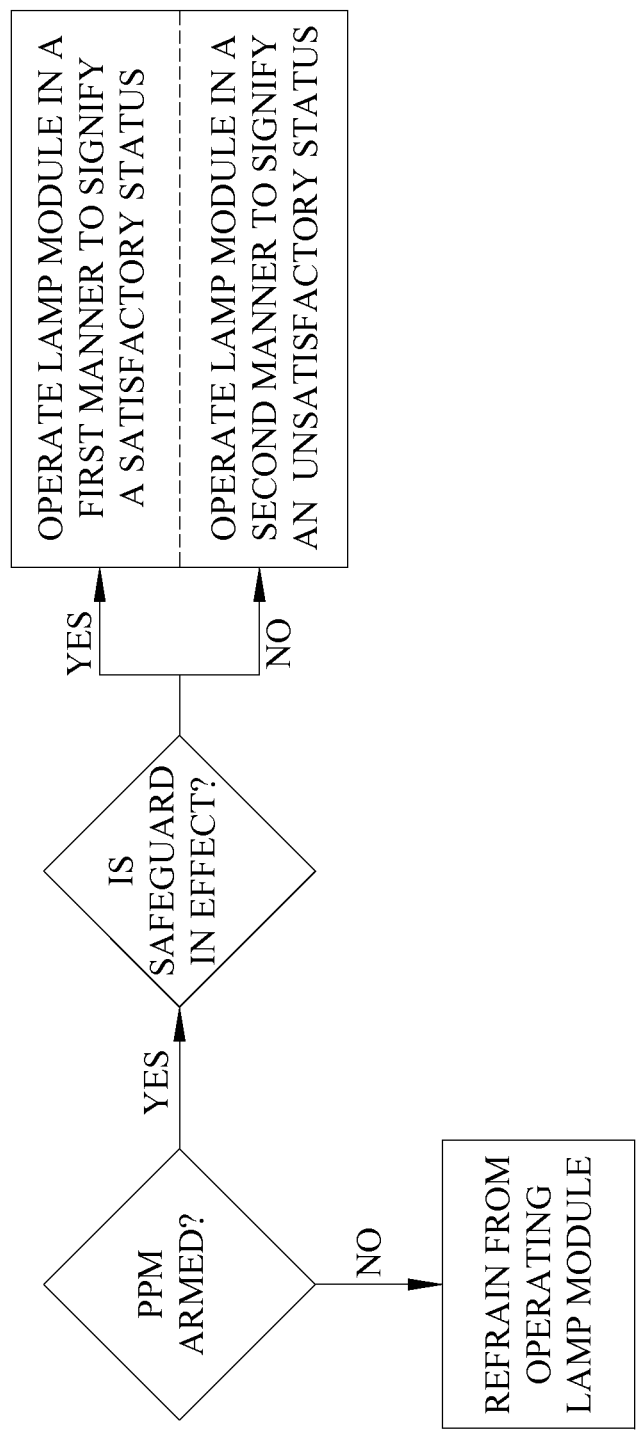
FIG. 4 is a block diagram showing decisions leading to operation of a lamp module in either a first or second manner depending on the state of the bed.
Figure 5:
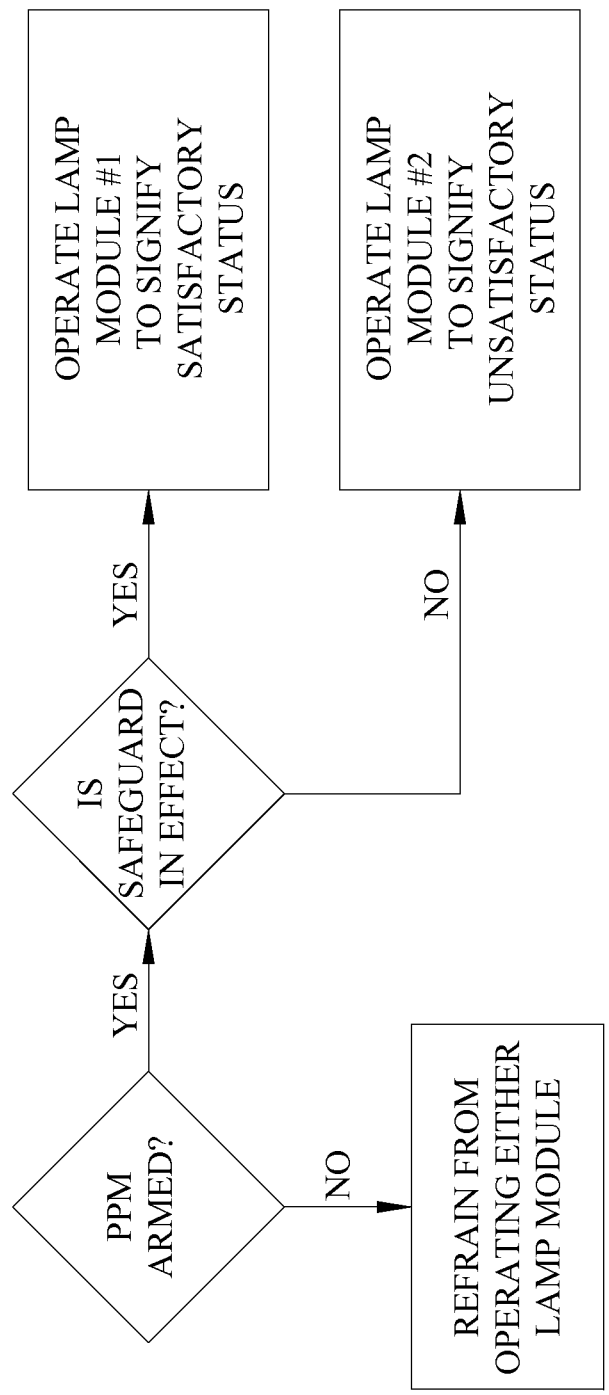
FIG. 5 is a view similar to that of FIG. 4 showing operation of one or the other of two dedicated lamp modules depending on the state of the bed.

Referring to FIG. 4, a method of reporting the status of a bed for an occupant at risk of falling includes determining if the PPM system is armed. If so, and if a fall risk safeguard is in effect, a lamp module 42 (FIGS. 1 and 2) is operated in a first manner to signify that the bed status is satisfactory. However if the PPM system is armed and a fall risk safeguard is not in effect, the lamp module 42 is operated in a second manner to signify that the bed status is unsatisfactory. If the PPM is not armed, the method refrains from operating the lamp module. The same lamp module is used to signify both the satisfactory bed status and the unsatisfactory bed status. As a result, the module is operated in a different manner depending on which status is to be signified. Preferably, the module emits green light to signify the satisfactory status and amber light to signify the unsatisfactory status. The light emission may be steady or intermittent or may be steady for one status and intermittent for the other. Preferably, the light emission corresponding to the satisfactory bed status is steady; the light emission corresponding to the unsatisfactory status is intermittent. The use of the same lamp module for both the satisfactory status indication and the unsatisfactory indication does not preclude the use of multiple such modules distributed about the bed as seen in FIG. 1. Alternatively, as suggested in FIG. 5, the lamp module operated to signify the satisfactory status and the lamp module operated to signify the unsatisfactory status may be different, mutually exclusive modules, one dedicated to the satisfactory status and one dedicated to the unsatisfactory status, with neither module being operated if the PPM system is disarmed. Because the dedicated modules are mutually exclusive, they can both be operated in the same manner (e.g. both emitting the same color light, at the same intensity and with the same degree of intermittency, including steady emission) or they may be operated in different manners as described above for the nondedicated lamp module. In addition, multiple sets of the dedicated modules may be deployed about the bed.

Referring to FIG. 6, certain components of a physical system related to the status reporting method includes the PPM system 60, at least one lamp module 42, an integrated circuit chip 64 containing lamp logic 62, and a printed circuit board (PCB) 66. The chip includes logic related to a number of functions of the bed including the logic 62 for determining whether the lamp module should indicate a satisfactory or unsatisfactory bed status. The PCB is in communication with the chip and, based on the determination from the logic 62, operates the lamp module to make the required indication. Collectively, the chip and PCB define a means 68 for conditionally governing operation of the lamp module based on inputs from the PPM system (armed or disarmed) and a determination of whether or not a safeguard is in effect as described above. The means 68 produces a SATISFACTORY message or signal to operate the lamp module in a first manner if the PPM is in its armed state and the safeguard is in effect. The means 68 produces an UNSATISFACTORY message or signal to operate the lamp module in a second manner if the PPM is in its armed state and the safeguard is not in effect. Depending on the results (SATISFACTORY OR UNSATISFACTORY) the lamp module is commanded to operate in a first manner to signify a satisfactory status of the bed or in a second manner to signify an unsatisfactory status of the bed. As illustrated, the lamp module operated in the first manner and the lamp module operated in the second manner are the same lamp module. The first manner of operation comprises operating the green LED's, 48 either steadily or intermittently but preferably steadily. The second manner of operation comprises operating the amber LED's 50 either steadily or intermittently, but preferably intermittently. However, in accordance with the method described above in the context of FIG. 5, the system could instead use different lamp modules, one dedicated to the satisfactory bed status and the other dedicated to the unsatisfactory bed status.

If the PPM is not armed, the occupant has not been identified as having an unacceptable risk of falling. Accordingly, the lamp module is operated in a third manner. Specifically, the method and system refrain from issuing a message or signal to operate the lamp module (or modules), resulting in non-emission of visible light from the lamp module. The non-issuance of a signal or message may be viewed as the issuance of a NULL message.

In some situations, the above described system and method may used on a bed already having other systems for alerting, alarming or otherwise indicating noncompliance with a desired state. One example of such an other system is a Head of Bed (HOB) alarm which sounds an audible alarm if the HOB alarm is armed and the Head of Bed angle α (FIG. 3) is determined to be less than 30 degrees. When the system disclosed above is used in conjunction with the other system, it is desirable for the above disclosed system to signal an unsatisfactory status under any conditions that cause or would cause the other system to issue an indication of noncompliance, even if the above disclosed system would otherwise indicate a satisfactory status.

Figure 7:
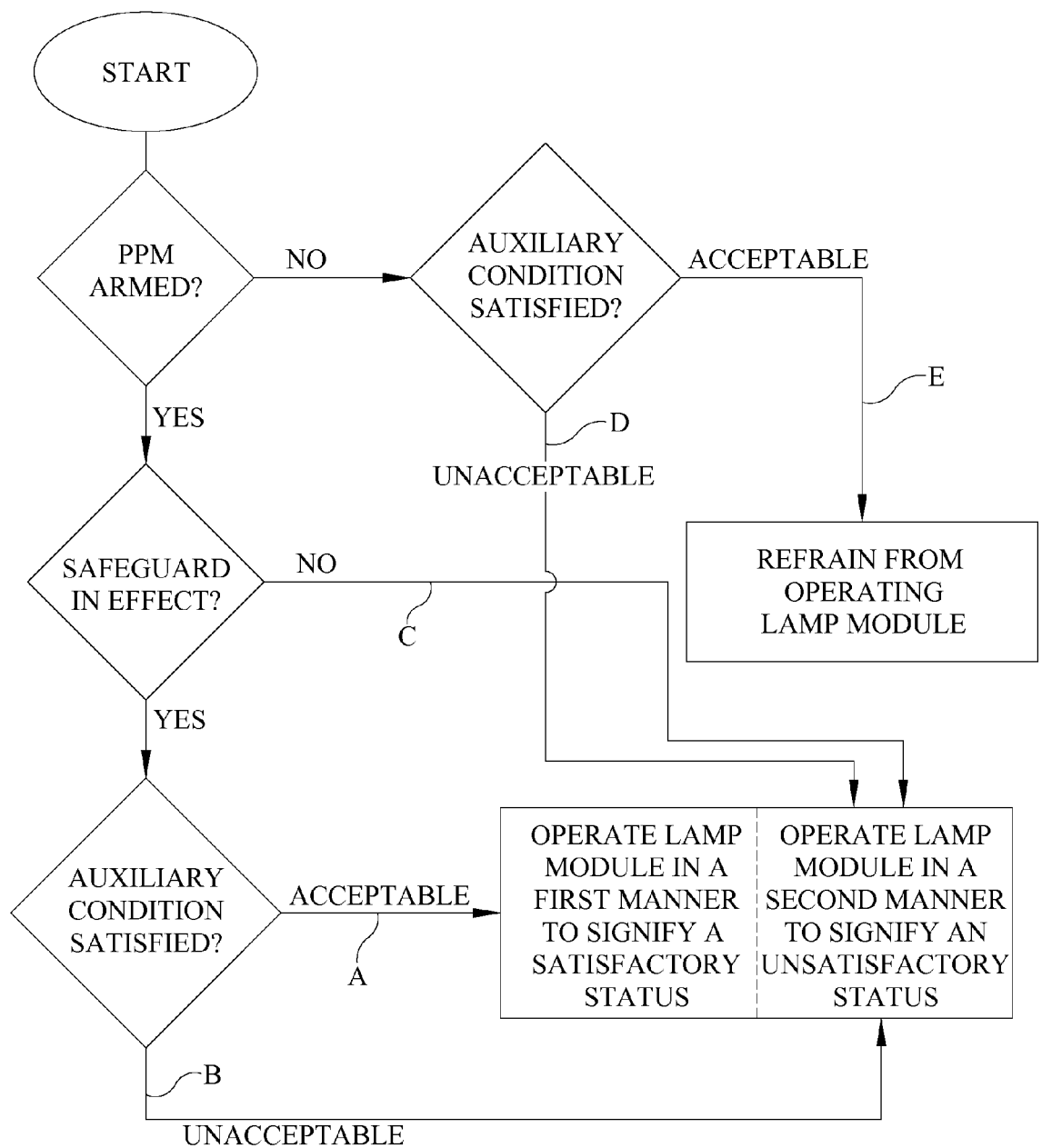
FIG. 7 is a view similar to that of FIG. 4 showing a method and system that uses an auxiliary condition for assessing the status of the bed.

FIG. 7 shows the combination of an auxiliary condition, such as whether or not the HOB angle is less than 30 degrees, with the method and system already described. As seen in the Figure, the method determines if the PPM is armed. If so, and if the safeguard is in effect (e.g. head end siderails deployed, height adjustable frame at its lowest position, brake set), the method determines if an auxiliary condition is acceptable (e.g. the HOB angle is at least 30 degrees). If the auxiliary condition is satisfied or acceptable (path A), the method operates a lamp module in the first manner to signify a satisfactory status of the bed. However if the auxiliary condition is not satisfied or unacceptable (path B), the method operates the lamp in the second manner to signify an unsatisfactory status of the bed. The system also operates the lamp in the second manner to indicate an unsatisfactory status if the PPM is armed and the safeguard is not in effect (path C) or if the auxiliary condition is unacceptable (i.e. the auxiliary condition isn't satisfied) even if the PPM system is not armed and irrespective of whether or not the safeguard is in effect (path D). The method indicates a NULL status if the PPM system is not armed and the state of the auxiliary condition is acceptable (path E).

Figure 8:
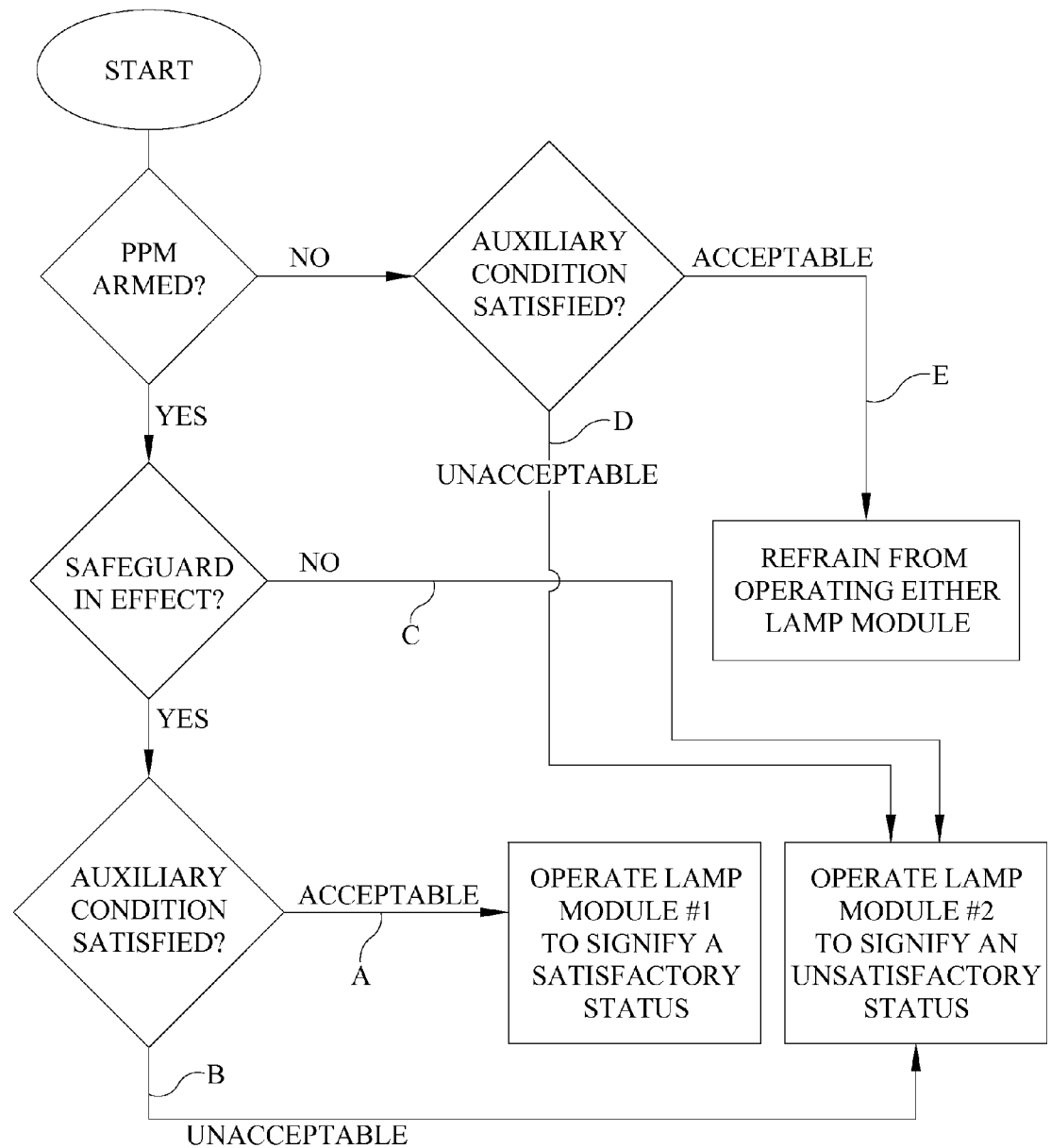
FIG. 8 is a view similar to that of FIG. 5 showing a method and system that uses an auxiliary condition for assessing the status of the bed.

FIG. 8 shows a method and system similar to that of FIG. 7, but using one lamp module dedicated to the satisfactory status and one dedicated to the unsatisfactory status.

Figure 9:
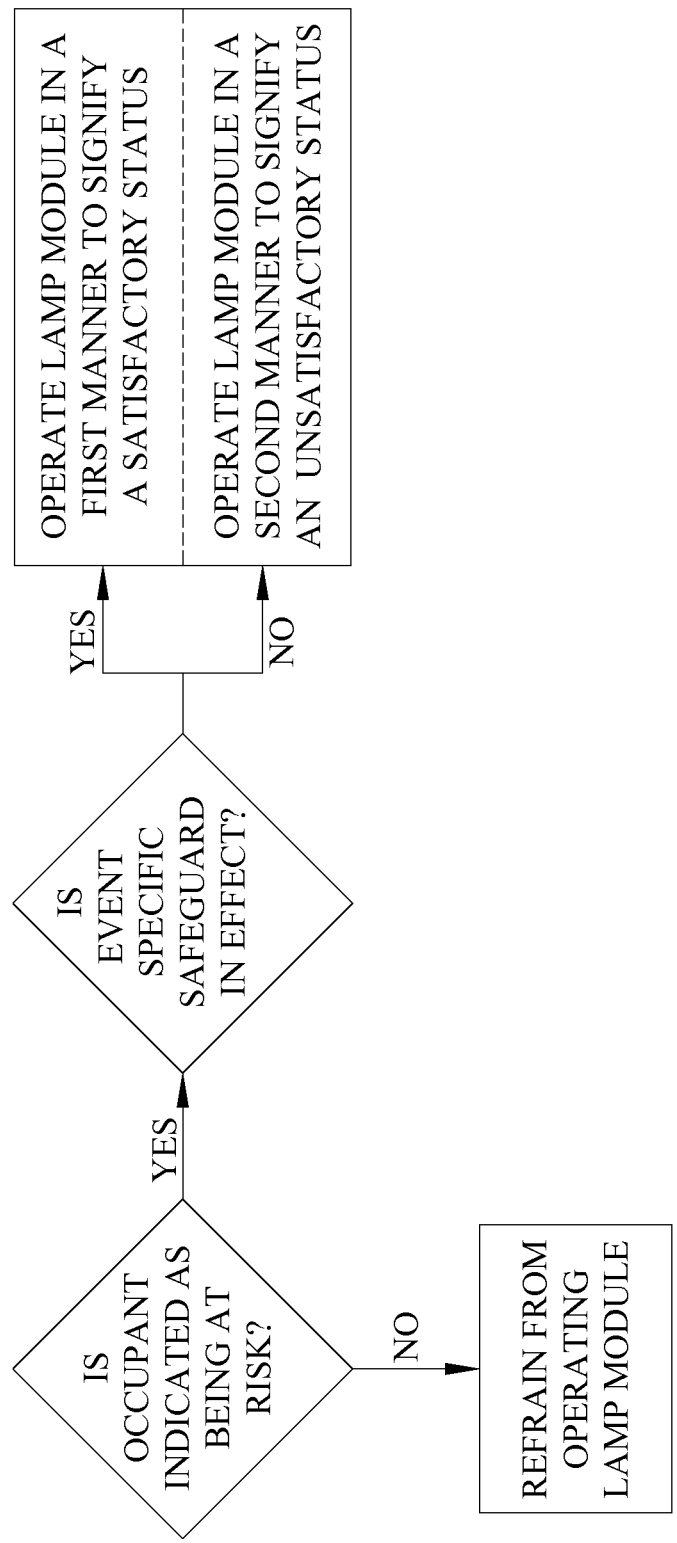
FIG. 9 is a view showing a generic version of the method and system of FIG. 4.
Figure 10:
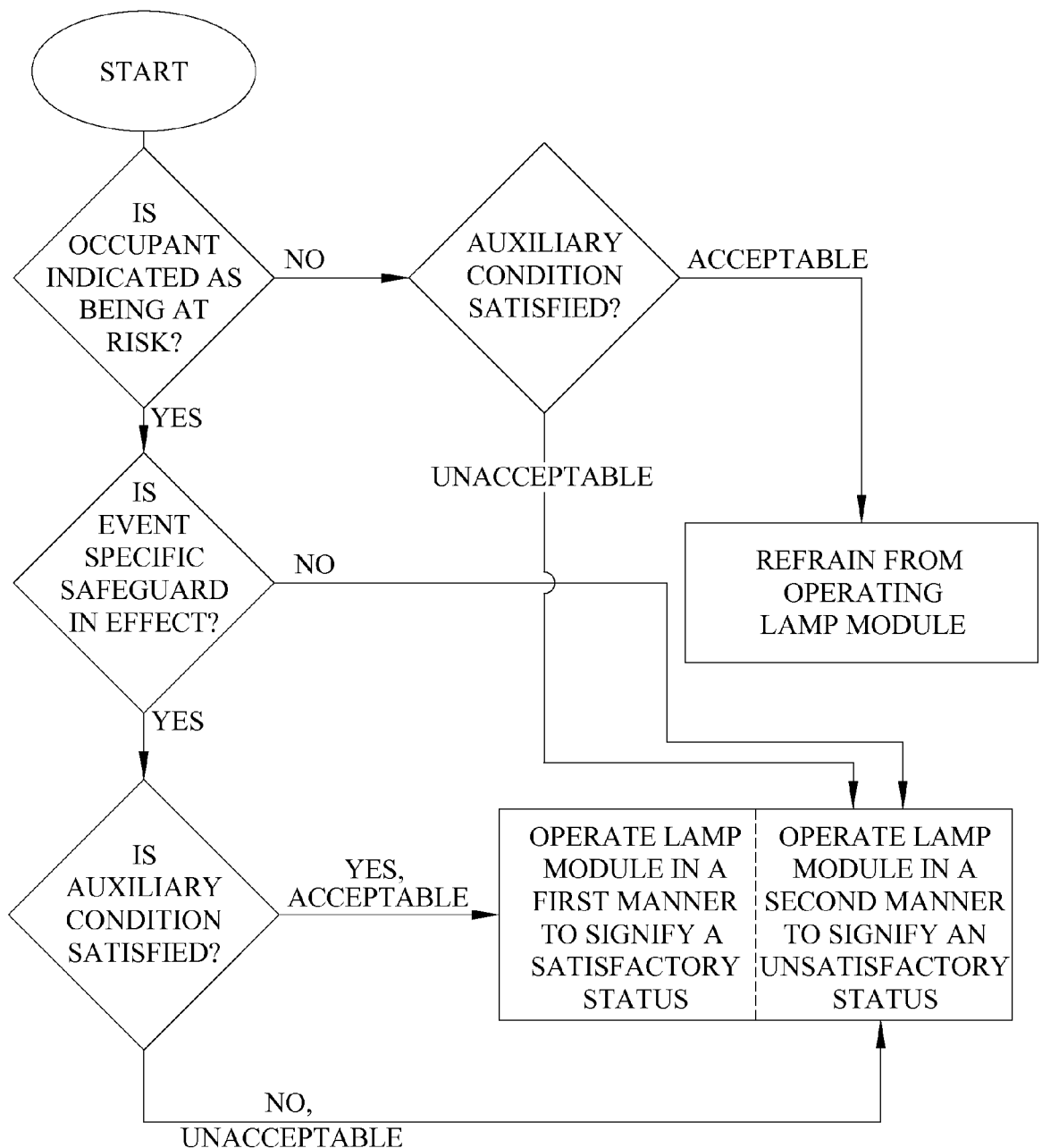
FIG. 10 is a view showing a generic version of the method and system of FIG. 7.

FIGS. 9 and 10 show the method and the associated system generalized to risks of undesired events other than falls. The generalization involves indicating that the bed occupant is at risk of the undesired event (for example arming a PPM system indicates that the bed occupant has an unacceptably high risk of falls) and determining if a safeguard specific to the risk is in effect. Whether or not a particular, risk specific safeguard is in effect will be a function of one or more states or conditions related to the risk in question. Referring specifically to FIG. 9 and the table below, if the occupant is indicated as being at risk and the risk specific safeguard is in effect, an indication is provided to signify a satisfactory status of the bed. If the occupant is indicated as being at risk and the risk specific safeguard is not in effect, an indication is provided to signify an unsatisfactory status as set forth below:

| At Risk? | Is Event Specific Safeguard In Effect? | Bed Status Indication |
| --- | --- | --- |
| Yes | Yes | Satisfactory |
| Yes | No | Unsatisfactory |

As seen in FIG. 10 and the table below, an auxiliary condition, such as the HOB angle, can also be accounted for.

| Auxiliary Condition | At Risk? | Is Event Specific Safeguard In Effect? | Bed Status Indication |
| --- | --- | --- | --- |
| Acceptable | Yes | Yes | Satisfactory |
| Acceptable | Yes | No | Unsatisfactory |
| Unacceptable | | | Unsatisfactory |

The system and method as illustrated in FIGS. 9 and 10 suggest the use of the same lamp module for signifying both the satisfactory and unsatisfactory states, however dedicated lamp modules, as previously described, can be employed instead. Moreover, it will be appreciated that variations on the theme, such as but not limited to those previously described (property of light emission, dedicated vs. non-dedicated lamp modules, the use of single or multiple lamp modules, and the use of an auxiliary condition) can be employed or not at the discretion of the designer.

Figure 11:
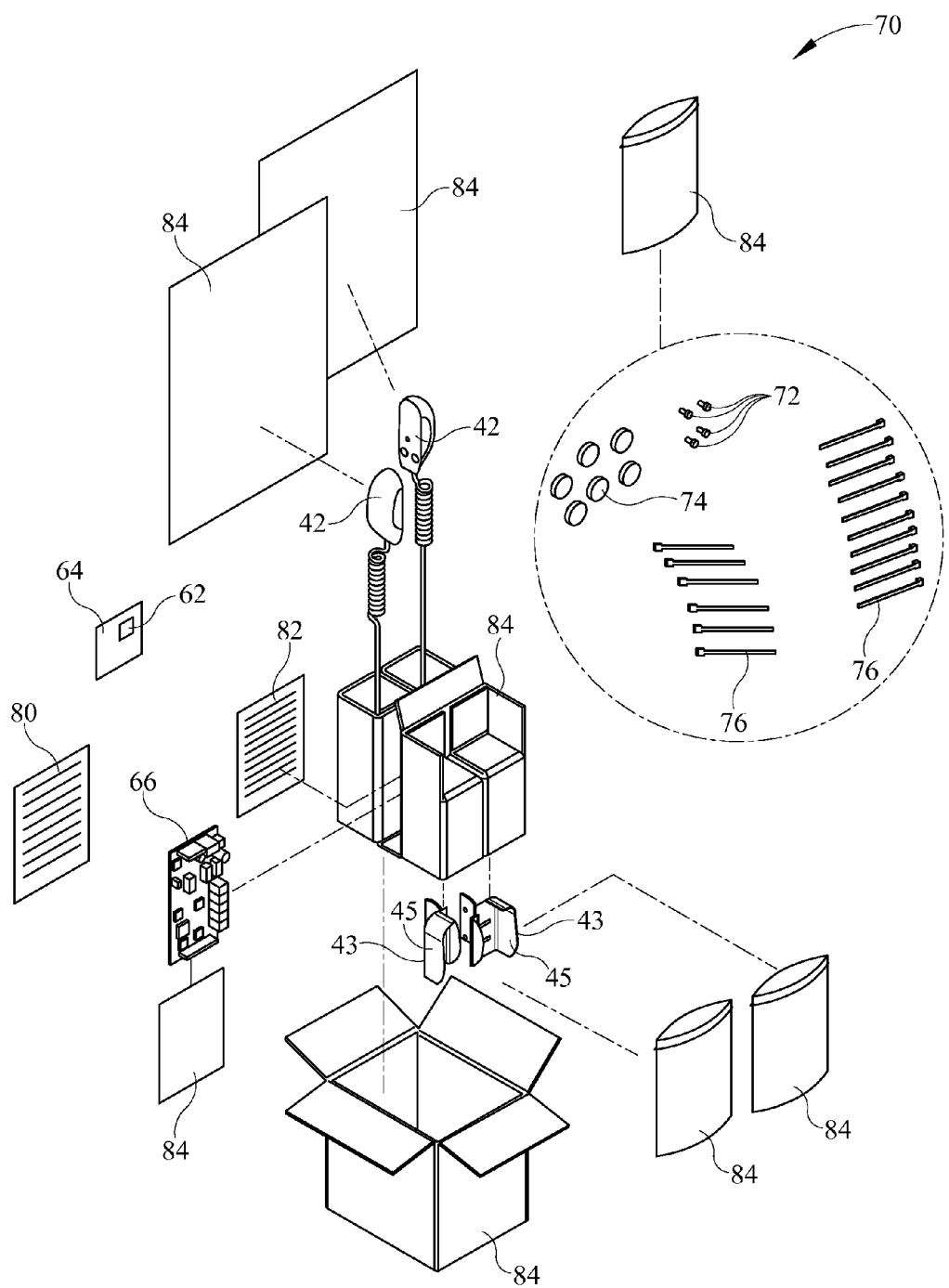
FIG. 11 is a schematic view of components of a retrofit kit for incorporating the reporting capability disclosed herein in a pre-existing bed.

The disclosed system may be included in newly manufactured beds, allowing those beds to carry out the disclosed method. The system may also be retrofit into pre-existing beds to upgrade their capabilities. Accordingly, as seen in FIG. 11, a retrofit kit 70 includes at least one lamp module 42 configured to be responsive the SATISFACTORY message, the UNSATISFACTORY message and the NULL message, and left and right brackets 43 for securing the lamp modules to the height adjustable frame 16. The kit also includes chip 64, PCB 66, various fasteners such as bracket screws 72, magnets 74 and cable ties 76 for securing the brackets and wires to a bed. The kit also includes labels 80, instructions 82 and packaging components 84. The chip 64 is substitutable for a pre-existing chip on the bed that does not have the lamp operating logic 62. Similarly, the PCB is substitutable for a pre-existing PCB on the bed that is not capable of operating the lamp modules. The lamp operating logic 62 is capable of receiving a Patient Position Monitoring (PPM) message from a PPM system indicating whether the PPM system is armed or disarmed and is also capable of receiving state or condition information for revealing whether a risk specific safeguard is in effect. The logic 62 and PCB 64 are responsive to the PPM message and the state or condition information for producing a SATISFACTORY or UNSATISFACTORY message as set forth below:

| PPM | Safeguard | Bed Status Indication |
| --- | --- | --- |
| Armed | In Effect | Satisfactory |
| Armed | Not In Effect | Unsatisfactory |

The method may also be used in conjunction with other systems designed to indicate noncompliance with a requirement. The logic 62 and PCB 64 are responsive to the PPM message, the state or condition information, and the auxiliary condition for producing a SATISFACTORY or UNSATISFACTORY message as set forth below:

| Auxiliary Condition | PPM | Safeguard | Bed Status Indication |
| --- | --- | --- | --- |
| Acceptable | Armed | In Effect | Satisfactory |
| Acceptable | Armed | Not In Effect | Unsatisfactory |
| Unacceptable | | | Unsatisfactory |

Although this disclosure refers to specific embodiments, it will be understood by those skilled in the art that various changes in form and detail may be made without departing from the subject matter set forth in the accompanying claims.

We claim:

1. A method of reporting the status of a bed for an occupant at risk of falls, comprising:
    determining if a Patient Position Monitoring (PPM) system is armed;
    determining if a safeguard is in effect; and
    operating a lamp module to signify a satisfactory status or an unsatisfactory status of the bed in response to the determining steps as set forth below:

| PPM | Safeguard | Bed Status |
| --- | --- | --- |
| Armed | In Effect | Satisfactory |
| Armed | Not In Effect | Unsatisfactory. |

2. The method of claim 1 wherein the safeguard is in effect only if all of one or more input conditions are satisfied.

3. The method of claim 2 wherein the input conditions to be satisfied include 1) a brake being set, 2) a height adjustable portion of the bed being at a lowest elevation, and 3) at least two laterally spaced apart siderails near the head end of the occupant being deployed.

4. The method of claim 1 wherein the safeguard is in effect if any one of one or more input conditions is satisfied.

5. The method of claim 4 wherein the input conditions to be satisfied include 1) a brake being set, 2) a height adjustable portion of the bed being at a lowest elevation, and 3) at least two laterally spaced apart siderails near the head end of the occupant being deployed.

6. The method of claim 1 including refraining from operating the lamp module if the PPM system is disarmed.

7. The method of claim 1 wherein the satisfactory status and the unsatisfactory status are distinguished from each other by a property of light emitted by the lamp module.

8. The method of claim 7 wherein the property of light is at least one of color and steadiness.

9. The method of claim 7 wherein the lamp module emits steady green light to signify the satisfactory status, the lamp module intermittently emits amber light to signify the unsatisfactory status and the lamp module emits substantially no visible light to signify that the PPM system is disarmed.

10. The method of claim 1 including a first lamp module dedicated to the satisfactory status, a second lamp module dedicated to the unsatisfactory status and wherein the satisfactory status is indicated by operating the first lamp module and the unsatisfactory status is indicated by operating the second lamp module.

11. The method of claim 10 wherein the satisfactory status and the unsatisfactory status are further distinguished from each other by a property of light emitted by the operated lamp module.

12. The method of claim 11 wherein the property of light is at least one of color and steadiness.

13. The method of claim 11 wherein the lamp module signifying the satisfactory status emits steady green light when operated and the lamp module signifying the unsatisfactory status intermittently emits amber light when operated.

14. The method of claim 1 wherein the lamp module is secured to the bed.

15. The method of claim 1 including:
determining if an auxiliary condition is acceptable or unacceptable; and
operating the lamp module to signify a satisfactory status or an unsatisfactory status of the bed in response to the determining steps as set forth below:

| Auxiliary Condition | PPM | Safeguard | Bed Status |
|---|---|---|---|
| Acceptable | Armed | In Effect | Satisfactory |
| Acceptable | Armed | Not In Effect | Unsatisfactory |
| Unacceptable | | | Unsatisfactory. |

16. The method of claim 1, wherein operating the lamp module includes directing light emitted from the lamp module at least partially toward a floor.

17. The method of claim 16 wherein the light is directed predominantly toward the floor.

18. The method of claim 15 wherein the lamp module is positioned and oriented so that light emitted from the module is directed at least partially toward a floor.

19. The method of claim 18 wherein the light is directed predominantly toward the floor.

20. A status reporting system for reporting whether or not an occupant of a bed is satisfactorily protected, comprising:
a Patient Position Monitoring (PPM) system having an armed state and a disarmed state;
at least one lamp module;
means responsive to the state of the PPM system and to a safeguard being in effect or not in effect for conditionally governing operation of the lamp module, the means producing a message to operate the lamp module in a first manner to signify a satisfactory status of the bed or a second manner to signify an unsatisfactory status of the bed as set forth below:

| PPM | Safeguard | Manner of Operation |
|---|---|---|
| Armed | In Effect | First |
| Armed | Not In Effect | Second. |

21. The system of claim 20 wherein the safeguard is in effect only if all of one or more input conditions are satisfied.

22. The system of claim 21 wherein the input conditions to be satisfied include 1) a brake being set, 2) a height adjustable portion of the bed being at a lowest elevation, and 3) at least two laterally spaced apart siderails near the head end of the occupant being deployed.

23. The system of claim 20 wherein the safeguard is in effect if any one of one or more input conditions is satisfied.

24. The system of claim 23 wherein the input conditions to be satisfied include 1) a brake being set, 2) a height adjustable portion of the bed being at a lowest elevation, and 3) at least two laterally spaced apart siderails near the head end of the occupant being deployed.

25. The system of claim 20 wherein the first manner is emission of visible light of a first color and the second manner is emission of visible light of a second color.

26. The system of claim 25 wherein one of the first and second manners of emission includes intermittent emission.

27. The system of claim 20 wherein the means also produces a message to operate the lamp module in a third manner if the PPM is in the disarmed state.

28. The system of claim 27 wherein the first manner is emission of visible light of a first color, the second manner is emission of visible light of a second color and the third manner is non-emission of visible light.

29. The system of claim 28 wherein one of the first and second manners of emission includes intermittent emission.

30. The system of claim 20 wherein the at least one lamp module includes multiple light emitters.

31. The status reporting system of claim 20 comprising:
determining if an auxiliary condition is acceptable or unacceptable; and
operating the lamp module in a first manner to signify a satisfactory status of the bed or a second manner to signify an unsatisfactory status of the bed in response to the state of the PPM system and to the safeguard being in effect or not in effect and to a status of an auxiliary condition as set forth below:

| Status of an Auxiliary Condition | PPM Status | Safeguard | Manner of Operation |
|---|---|---|---|
| Acceptable | Armed | In Effect | First |
| Acceptable | Armed | Not In Effect | Second |
| Unacceptable | | | Second. |

32. The system of claim 20 including a shield for intercepting light emissions in directions toward occupants of nearby beds.

33. A method of reporting the status of a bed whose occupant is at risk of an undesired event, comprising:
indicating that the occupant is at risk of the undesired event; and
operating a lamp module to signify a satisfactory status or an unsatisfactory status of the bed in response to the risk indication and to an event specific safeguard being in effect or not in effect as set forth below:

| At Risk? | Is Event Specific Safeguard In Effect? | Bed Status |
|---|---|---|
| Yes | Yes | Satisfactory |
| Yes | No | Unsatisfactory. |

34. The method of claim 33 wherein arming of an occupant monitoring system indicates that the occupant is at risk and the event specific safeguard includes at least one physical condition of the bed.

35. The method of claim 33 including:
determining if an auxiliary condition is satisfied or unsatisfied; and
providing an indication to signify a satisfactory or unsatisfactory status of the bed in response to the risk indication and to an event specific safeguard being in effect or not in effect, and to a status of an auxiliary condition as set forth below:

| Auxiliary Condition | At Risk? | Is Event Specific Safeguard In Effect? | Bed Status |
|---|---|---|---|
| Acceptable | Yes | Yes | Satisfactory |
| Acceptable | Yes | No | Unsatisfactory |
| Unacceptable | | | Unsatisfactory. |

36. A retrofit kit for upgrading a bed to reveal whether or not an occupant of the bed is satisfactorily protected, comprising:
at least one lamp module securable to the bed and configured to be responsive a SATISFACTORY message, an UNSATISFACTORY message and a NULL message; means, responsive to a PPM message indicating whether a PPM system is armed or disarmed and also responsive to state or condition information for revealing whether a risk specific safeguard is in effect for producing the SATISFACTORY or UNSATISFACTORY message as set forth below:

| PPM State | Risk Specific Safeguard | Message |
|---|---|---|
| Armed | In Effect | SATISFACTORY |
| Armed | Not In Effect | UNSATISFACTORY. |

37. The retrofit kit of claim 36 wherein the means includes:
a chip substitutable for a pre-existing chip on the bed; and
a Printed Circuit Board (PCB) board substitutable for a pre-existing PCB on the bed.

38. The retrofit kit of claim 36 wherein the means is also responsive to an auxiliary condition being acceptable or unacceptable and produces a satisfactory or unsatisfactory message as set forth below:

| Auxiliary Condition | PPM Status | Risk Specific Safeguard | Message |
|---|---|---|---|
| Acceptable | Armed | In Effect | Satisfactory |
| Acceptable | Armed | Not In Effect | Unsatisfactory |
| Unacceptable | | | Unsatisfactory. |

* * * * *